United States Patent
Makino et al.

(10) Patent No.: US 11,312,935 B2
(45) Date of Patent: Apr. 26, 2022

(54) CELL CULTURE SYSTEM, CELL CULTURE ENVIRONMENT EVALUATION DEVICE, AND PROGRAM

(71) Applicant: NIHON KOHDEN CORPORATION, Tokorozawa (JP)

(72) Inventors: Hodaka Makino, Tokorozawa (JP); Wataru Matsuzawa, Tokorozawa (JP)

(73) Assignee: Nihon Kohden Corporation, Tokorozawa (JP)

( * ) Notice: Subject to any disclaimer, the term of this patent is extended or adjusted under 35 U.S.C. 154(b) by 199 days.

(21) Appl. No.: 15/854,696

(22) Filed: Dec. 26, 2017

(65) Prior Publication Data

US 2018/0371396 A1    Dec. 27, 2018

(30) Foreign Application Priority Data

Jan. 20, 2017   (JP) .............................. JP2017-008942

(51) Int. Cl.
*C12M 1/34*       (2006.01)
*C12M 1/36*       (2006.01)
(Continued)

(52) U.S. Cl.
CPC ............ *C12M 41/00* (2013.01); *C12M 33/00* (2013.01); *C12M 41/12* (2013.01); *C12M 41/14* (2013.01);
(Continued)

(58) Field of Classification Search
CPC ...... C12M 41/00; C12M 41/14; C12M 41/48; C12M 41/36; C12M 41/34; C12M 41/26; C12M 41/12; C12M 33/003
See application file for complete search history.

(56) References Cited

U.S. PATENT DOCUMENTS

| | | | |
|---|---|---|---|
| 6,673,008 B1* | 1/2004 | Thompson | A01K 45/007 435/290.4 |
| 2002/0055166 A1* | 5/2002 | Cannon | C12M 23/42 435/286.5 |

(Continued)

FOREIGN PATENT DOCUMENTS

| | | |
|---|---|---|
| EP | 2484750 A1 | 8/2012 |
| EP | 2489435 A2 | 8/2012 |

(Continued)

OTHER PUBLICATIONS

Extended European Search Report received for EP application 18150997.7-1132 dated Jun. 19, 2018.

(Continued)

*Primary Examiner* — Michael L Hobbs
(74) *Attorney, Agent, or Firm* — Dorsey & Whitney LLP (57) ABSTRACT

An object of the present disclosure is to provide a cell culture system, a cell culture environment evaluation device, and a program, capable of performing evaluation of a culture environment without causing an adverse effect on cell culture. An isolator is provided with a culture environment for housing a cell culture vessel having a culture solution containing cells to be cultured placed therein. A sensing unit measures the state of the culture environment and transmits the measurement result of the culture environment to the outside of the isolator. A control device receives the measurement result and performs evaluation in the culture environment based on the measurement result.

12 Claims, 9 Drawing Sheets

(51) Int. Cl.
 *C12M 1/26* (2006.01)
 *C12M 1/00* (2006.01)
(52) U.S. Cl.
 CPC ............ *C12M 41/26* (2013.01); *C12M 41/34* (2013.01); *C12M 41/36* (2013.01); *C12M 41/48* (2013.01)

(56) References Cited

U.S. PATENT DOCUMENTS

| | | | | |
|---|---|---|---|---|
| 2005/0105172 | A1* | 5/2005 | Hasegawa | C12M 23/50 359/368 |
| 2008/0318307 | A1 | 12/2008 | Spittle et al. | |
| 2010/0009335 | A1* | 1/2010 | Joseph | C12M 23/12 435/3 |
| 2012/0214225 | A1 | 8/2012 | Oura et al. | |
| 2013/0038727 | A1 | 2/2013 | Clark | |
| 2013/0316442 | A1* | 11/2013 | Meurville | C12M 41/00 435/287.5 |

FOREIGN PATENT DOCUMENTS

| | | |
|---|---|---|
| EP | 2505635 A1 | 10/2012 |
| JP | H04040885 A | 2/1992 |
| JP | H10512159 A | 11/1998 |
| JP | 2006055027 A | 3/2006 |
| JP | 2007222083 A | 9/2007 |
| JP | 2009180594 A | 8/2009 |
| JP | 2009533053 A | 9/2009 |
| JP | 2012170358 A | 9/2012 |
| JP | 2012200239 A | 10/2012 |
| JP | 2013516999 A | 5/2013 |
| WO | 9716527 A1 | 5/1997 |
| WO | 03104386 A1 | 12/2003 |
| WO | 2007120619 A2 | 10/2007 |
| WO | 2011090792 A1 | 7/2011 |

OTHER PUBLICATIONS

English translation of Notice of Reasons for Refusal for JP Application No. 2017-008942, dated Oct. 6, 2020.

Kubo, Hirotsugu, "Regenerative Medicine Opened by an Automatic Primary Culture Device", The Japanese Journal of Medical Instrumentation, vol. 81, No. 6, Feb. 27, 2012, pp. 439-445.

Kubo, Hirotsugu, "Significance of Culture Environment Monitoring: Non-Contact and Sampling Methods", The Japanese Journal of Medical Instrumentation, vol. 85, No. 4, Oct. 15, 2015, pp. 407-411.

Oura, M. et al., "Development of Cell Culture Monitoring System and Novel Non-Contact pH Measurement", 33rd Annual International conference of the IEEE EMBS, Aug. 30-Sep. 3, 2011, pp. 22-25.

English translation of Office Action for JP Application No. 2017-008942, dated Apr. 2, 2021.

* cited by examiner

| EVENT | CHANGE IN pH |
|---|---|
| GENERATION OF LACTIC ACID (NORMAL STATE) | DECREASE |
| CONTAMINATION | RAPID DECREASE |
| ABNORMALITY IN OPENING AND CLOSING OF DOOR, ABNORMALITY IN GAS SUPPLY | INCREASE |

FIG. 3B

| EVENT | CHANGE IN TEMPERATURE |
|---|---|
| OPENING AND CLOSING OF DOOR | DECREASE |

FIG. 3C

| EVENT | CHANGE IN $CO_2$ CONCENTRATION |
|---|---|
| OPENING AND CLOSING OF DOOR | DECREASE |
| SUPPLY SHORTAGE OF $CO_2$ GAS | DECREASE |

FIG. 3D

| EVENT | CHANGE IN TURBIDITY |
|---|---|
| CONTAMINATION | RAPID INCREASE |
| IMMEDIATELY AFTER CELL SEEDING (NORMAL) | DECREASE |

FIG. 4A

| pH | DETERMINATION OF STATE | FACTOR |
|---|---|---|
| INCREASE | ABNORMAL | OPENING AND CLOSING OF OPENING AND CLOSING DOOR OR SHORTAGE OF GAS |
| RAPID DECREASE | ABNORMAL | CONTAMINATION |
| DECREASE | - | NORMAL CULTURE (GENERATION OF LACTIC ACID) |

FIG. 4B

| TEMPERATURE | DETERMINATION OF STATE | FACTOR |
|---|---|---|
| DECREASE | ABNORMAL | OPENING AND CLOSING OF OPENING AND CLOSING DOOR |
| WITHIN GIVEN RANGE | - | - |

FIG. 4C

| $CO_2$ | DETERMINATION OF STATE | FACTOR |
|---|---|---|
| DECREASE | ABNORMAL | OPENING AND CLOSING OF OPENING AND CLOSING DOOR OR SHORTAGE OF GAS |
| WITHIN GIVEN RANGE | - | - |

FIG. 5A

| TURBIDITY | DETERMINATION OF STATE | FACTOR |
|---|---|---|
| RAPID INCREASE | ABNORMAL | IMMEDIATELY AFTER CELL SEEDING |
| DECREASE | - | CONTAMINATION |
| WITHIN GIVEN RANGE | - | - |

FIG. 5B

| pH | TEMPERATURE | DETERMINATION OF STATE | FACTOR |
|---|---|---|---|
| INCREASE | DECREASE | ABNORMAL | OPENING AND CLOSING OF OPENING AND CLOSING DOOR |
| INCREASE | WITHIN GIVEN RANGE | ABNORMAL | SHORTAGE OF GAS |
| RAPID DECREASE | WITHIN GIVEN RANGE | ABNORMAL | CONTAMINATION |
| DECREASE | WITHIN GIVEN RANGE | - | - |

FIG. 6A

| pH | TURBIDITY | DETERMINATION OF STATE | FACTOR |
|---|---|---|---|
| INCREASE | WITHIN GIVEN RANGE | ABNORMAL | OPENING AND CLOSING OF OPENING AND CLOSING DOOR OR SHORTAGE OF GAS |
| RAPID DECREASE | RAPID INCREASE | ABNORMAL | CONTAMINATION |
| DECREASE | WITHIN GIVEN RANGE | - | - |
| DECREASE | DECREASE | IMMEDIATELY AFTER CELL SEEDING | - |

FIG. 6B

| $CO_2$ | TURBIDITY | DETERMINATION OF STATE | FACTOR |
|---|---|---|---|
| DECREASE | WITHIN GIVEN RANGE | ABNORMAL | OPENING AND CLOSING OF OPENING AND CLOSING DOOR OR SHORTAGE OF GAS |
| WITHIN GIVEN RANGE | RAPID INCREASE | ABNORMAL | CONTAMINATION |
| WITHIN GIVEN RANGE | WITHIN GIVEN RANGE | - | - |
| WITHIN GIVEN RANGE | DECREASE | IMMEDIATELY AFTER CELL SEEDING | - |

FIG. 7

| pH | TEMPERATURE | TURBIDITY | DETERMINATION OF STATE | FACTOR |
|---|---|---|---|---|
| INCREASE | DECREASE | WITHIN GIVEN RANGE | ABNORMAL | OPENING AND CLOSING OF OPENING AND CLOSING DOOR |
| INCREASE | WITHIN GIVEN RANGE | WITHIN GIVEN RANGE | ABNORMAL | SHORTAGE OF GAS |
| RAPID DECREASE | WITHIN GIVEN RANGE | RAPID INCREASE | ABNORMAL | CONTAMINATION |
| DECREASE | WITHIN GIVEN RANGE | WITHIN GIVEN RANGE | - | NORMAL PROLIFERATION |
| DECREASE | WITHIN GIVEN RANGE | DECREASE | - | IMMEDIATELY AFTER CELL SEEDING (NORMAL) |

FIG. 8

| pH | TEMPERATURE | CO₂ | TURBIDITY | DETERMINATION OF STATE | FACTOR |
|---|---|---|---|---|---|
| INCREASE | DECREASE | DECREASE | WITHIN GIVEN RANGE | ABNORMAL | OPENING AND CLOSING OF OPENING AND CLOSING DOOR |
| INCREASE | WITHIN GIVEN RANGE | DECREASE | WITHIN GIVEN RANGE | ABNORMAL | SHORTAGE OF GAS |
| RAPID DECREASE | WITHIN GIVEN RANGE | WITHIN GIVEN RANGE | RAPID INCREASE | ABNORMAL | CONTAMINATION |
| DECREASE | WITHIN GIVEN RANGE | WITHIN GIVEN RANGE | WITHIN GIVEN RANGE | - | NORMAL PROLIFERATION |
| DECREASE | WITHIN GIVEN RANGE | WITHIN GIVEN RANGE | DECREASE | - | IMMEDIATELY AFTER CELL SEEDING (NORMAL) | ns

CELL CULTURE SYSTEM, CELL CULTURE ENVIRONMENT EVALUATION DEVICE, AND PROGRAM

CROSS-REFERENCE TO RELATED APPLICATIONS

This application claims priority to Japanese Patent Application No. 2017-008942, filed Jan. 20, 2017, which is incorporated by reference herein, in its entirety and for all purposes.

TECHNICAL FIELD

The present disclosure relates to a cell culture system, a cell culture environment evaluation device, and a program.

BACKGROUND

In the field of regenerative medicine, artificial fertilization, or the like, there have been proposed various culture devices and sampling devices to be used for culture or sampling of cells (WO 2003/104386 (Patent Document 1), JP-A-2009-180594 (Patent Document 2), and JP-A-2012-200239 (Patent Document 3)).

In a cell culture device (or a sampling device), in order to maintain the inside of the culture environment in a sterile state, it is necessary to isolate the culture environment from the outside. For example, Patent Document 3 discloses a configuration for preventing contamination of a sterile space when performing sampling. A cell culture device described in Patent Document 3 includes an isolator provided with a sterile space for housing a cell culture vessel containing a culture solution, a sampling unit for sampling the culture solution, and a delivery channel for making the inside and the outside of the sterile space communicate with each other. Then, the cell culture device includes a culture solution delivery section for delivering the culture solution to the outside of the sterile space while limiting the direction of the flow in the delivery channel to the direction from the inside to the outside of the sterile space. According to the configuration, a contaminant generated in a non-sterile space can be prevented from penetrating into the sterile space, and a safe cell culture environment can be realized.

As described above, in a cell culture device (or a sampling device), it is important to maintain the inside of the culture environment in a sterile state. Due to this, it was necessary to monitor whether or not an abnormality occurs in the sterile space in which a cell culture vessel is placed. Then, in a general monitoring method, it was necessary to detect an abnormality by taking out the cell culture vessel from the sterile space and confirming the color of the culture medium or observing the state of cells using a microscope.

However, in the above-mentioned monitoring method, the cell culture vessel is placed in the external environment when it is taken out from the sterile space, and therefore, a large stress is applied to the cells, and therefore, there is a fear that an adverse effect on the cell culture is caused. Further, there is also a fear that the sterility of the sterile space is impaired.

SUMMARY

One aspect of a cell culture system according to the present disclosure includes:

a culture vessel housing chamber which is provided with a culture environment for housing a cell culture vessel having a culture solution containing cells to be cultured placed therein;

a sensing unit which measures the state of the culture environment and transmits the measurement result of the culture environment to the outside of the culture vessel housing chamber; and a control device which receives the measurement result and performs evaluation in the culture environment based on the measurement result.

As described above, the sensing unit measures the state of the culture environment in the culture vessel housing chamber and transmits the measurement result. The control device performs evaluation of the culture environment based on the measurement result. That is, the control device can perform evaluation in the culture environment without taking out the cell culture vessel from the culture vessel housing chamber. According to this, the cell culture system can perform evaluation in the culture environment without applying a stress to the cells during culture.

The present disclosure can provide a cell culture system, a cell culture environment evaluation device, and a program, capable of performing evaluation of a culture environment without causing an adverse effect on cell culture.

DETAILED DESCRIPTION

First Embodiment

Figure 1:
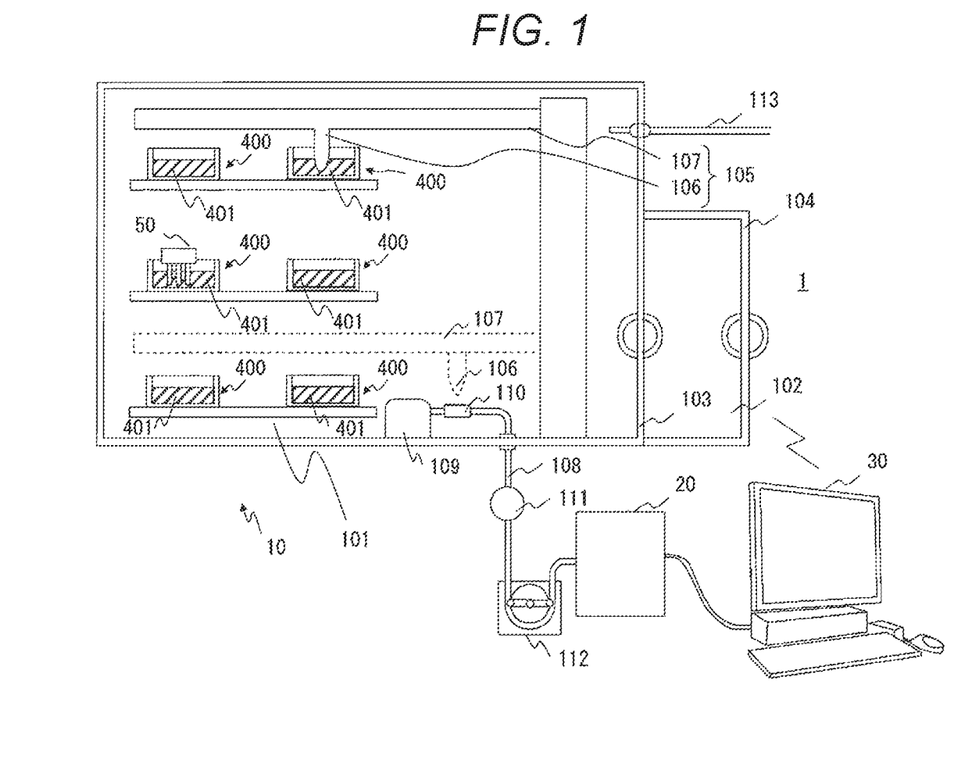
FIG. 1 is a block diagram showing the configuration of a cell culture system 1 according to a first embodiment.

Hereinafter, embodiments of the present disclosure will be described with reference to the drawings. FIG. 1 is a diagram showing the configuration of a cell culture system 1 according to a first embodiment. The cell culture system 1 includes an isolator 10, a measuring device 20, and a control device 30.

The isolator 10 includes a sterile chamber 101 and a pass box 102. The isolator 10 is one embodiment of a culture vessel housing chamber (an environment for housing a cell culture vessel having a culture solution containing cells to be cultured placed therein). The sterile chamber 101 is controlled so that the internal space thereof becomes a sterile space maintained at a sterile level suitable for culture. The sterile space (that is, the inside of the sterile chamber 101) becomes a cell culture environment. The sterile chamber 101 and the pass box 102 are openably and closably separated from each other with an opening and closing door 103. The pass box 102 is openably and closably separated from the internal space of the sterile chamber 101, and also openably and closably separated from the external space (a non-sterile space) with an opening and closing door 104. Incidentally, the isolator 10 may have another arbitrary configuration as long as it is configured such that the sterile chamber 101 is separated from the outside with the opening and closing door 103.

In the internal space of the sterile chamber 101, a plurality of cell culture vessels 400 each having a culture solution 401 placed therein are housed. In the culture solution 401, cells to be cultured are contained. Further, in the internal space of the sterile chamber 101, a sampling unit 105 for sampling the culture solution 401 in each cell culture vessel 400 is provided. The sampling unit 105 includes an injection port 106 which sucks and discharges the culture solution 401 of the cell culture vessel 400 to be sampled, and a conveying device 107 which conveys the injection port 106.

A sensing unit 50 which will be described later with reference to FIG. 2 measures the state of the cell culture vessel 400 (the hydrogen-ion exponent (pH), the temperature, the carbon dioxide concentration, and the turbidity of the culture solution 401, etc.). Incidentally, an arbitrary number of sensing units 50 may be provided in the isolator 10.

The internal space of the sterile chamber 101 communicates with the outside through a delivery channel 108. Incidentally, when the inside of the sterile chamber 101 is sterilized with a chemical agent, the material of the delivery channel 108 is a material with extremely low reactivity with the chemical agent.

The delivery channel 108 is connected to a buffer substance supply section 109 provided in the culture environment for supplying a buffer substance to the delivery channel 108. In the vicinity of an end portion in the sterile chamber 101 of the delivery channel 108, a discharge section 110 whose upper side is open is provided. On the other hand, an end portion on the external space side of the delivery channel 108 is connected to the measuring device 20. Further, on the channel on the external space side of the delivery channel 108, a one-way valve 111 and a peristaltic pump 112 are provided in this order from the side closer to the sterile chamber 101. Incidentally, as the peristaltic pump 112, another embodiment may be adopted as long as it can suck the culture solution 401.

The one-way valve 111 is a backflow prevention valve which blocks only the flow from the external space to the sterile chamber 101. The peristaltic pump 112 allows a fluid flowing in the delivery channel 108 from the inside of the sterile chamber 101 to flow to the measuring device 20 side.

A carbon dioxide supply channel 113 continuously supplies carbon dioxide gas so that the culture environment (the internal space of the sterile chamber 101) has a constant carbon dioxide concentration (for example, 5%).

Although not shown in the drawing, the isolator 10 includes an air conditioner to be used for keeping the inside of the isolator 10 at a temperature suitable for cell culture. The air conditioner performs temperature control (control of blowing hot air or cold air according to the temperature inside the isolator 10 detected by a temperature sensor) so that the temperature in the isolator 10 is comparable to human body temperature (35 to 37° C.). Incidentally, the air conditioner may be configured so that it can be controlled wirelessly from the outside of the isolator 10.

The measuring device 20 performs various measurements with respect to a fluid (the below-mentioned sampled culture solution) flowing from the delivery channel 108, and inputs the measurement results to the control device 30. The measuring device 20 measures, for example, the pH, the dissolved oxygen concentration, the glucose content, etc. of the sampled culture solution.

The control device 30 includes a device body, various input devices (a key board, a mouse, etc.), a display, etc. The control device 30 displays the measurement results input from the measuring device 20 or information such as setting of the measuring device 20 on the display. Further, the control device 30 receives an instruction of setting change or the like through the input device and outputs the instruction to the measuring device 20.

Further, the control device 30 operates as one embodiment of a cell culture environment evaluation device which receives the measurement results (pH, carbon dioxide concentration, temperature, turbidity, etc.) showing the state in the sterile chamber 101 (culture environment) from the below-mentioned sensing unit 50, and evaluates the state of the culture environment. The details of the evaluation of the culture environment by the control device 30 will be described later with reference to FIGS. 4A to 8.

The control device 30 gives a notification by an arbitrary method when an abnormality in the culture environment is detected by the below-mentioned evaluation system shown in FIGS. 4A to 8. For example, the control device 30 may output an alarm sound through a speaker or may display an alarm message indicating that an abnormality occurs on the display. Further, the control device 30 may change the notification method according to the type of detected abnormality (supply shortage of carbon dioxide gas, contamination, opening and closing of the opening and closing door 103, etc.). That is, the control device 30 may change the type of notification sound according to the type of abnormality, and may change the alarm message (for example, the type of abnormality may be displayed on the display).

Further, the control device 30 may give a notification by illuminating a built-in indicator or an indicator provided in a communicable manner, or the like. The control device 30 can also give a notification of the occurrence of an abnormality in the culture environment by email.

Hereinafter, one example of a sampling method of the culture solution 401 in the cell culture vessel 400 will be described. First, a buffer substance is allowed to continuously flow through the delivery channel 108 from the buffer substance supply section 109. Here, the buffer substance to be supplied from the buffer substance supply section 109 is preferably, for example, a liquid such as pure water subjected to a sterilization treatment or a gas subjected to a sterilization treatment. Subsequently, the injection port 106 is conveyed by the conveying device 107 to the cell culture vessel 400 to be sampled, and sucks the culture solution 401 in the cell culture vessel 400 by the injection port 106.

The injection port 106 after completion of suction is conveyed immediately above the discharge section 110 by the conveying device 107. The injection port 106 discharges the sucked culture solution 401 toward the discharge section 110. The culture solution 401 (hereinafter referred to as "sampled culture solution") discharged to the discharge section 110 here is delivered to the outside of the sterile chamber 101 by the buffer substance continuously flowing in the delivery channel 108. Then, the sampled culture solution is supplied to the measuring device 20 through the one-way valve 111 and the peristaltic pump 112.

Incidentally, in the configuration shown in FIG. 1, the measuring device 20 and the control device 30 are described as separate devices, however, the configuration is not necessarily limited thereto. That is, a configuration in which the control device 30 is connected to the delivery channel 108 and performs various measurements (the pH, the dissolved oxygen concentration, the glucose content, etc. of the sampled culture solution) to be performed by the measuring device 20 may be adopted.

Figure 2:
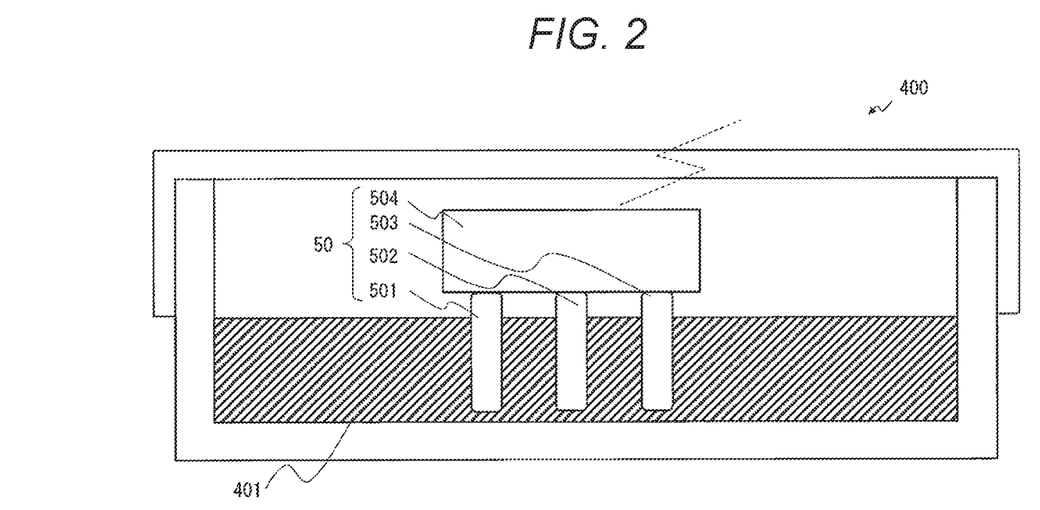
FIG. 2 is a conceptual view showing a configuration example of a sensing unit 50 according to the first embodiment.

FIG. 2 is a conceptual view showing a configuration example of the sensing unit 50 which measures the culture environment (the internal space of the sterile chamber 101). The sensing unit 50 is a device which measures the state of the culture environment and transmits the measurement result of the culture environment to the outside of the isolator 10 (control device 30). The sensing unit 50 shown in FIG. 2 includes a pH/turbidity sensor 501, a carbon dioxide sensor 502, a temperature sensor 503, and a device body 504.

The pH/turbidity sensor 501 is a sensor which measures the pH and the turbidity of the culture solution 401. The pH/turbidity sensor 501 performs general pH measurement, and at this time, also measures the turbidity. The pH/turbidity sensor 501 continuously measures the pH and the turbidity, and transmits the measurement results to the device body 504.

The carbon dioxide sensor 502 measures the carbon dioxide concentration in the environment (in the example shown in FIG. 2, in the culture solution 401) where the cell culture vessel 400 is placed. The carbon dioxide sensor 502 may be a general carbon dioxide measuring device (for example, a measuring device based on an infrared absorbance). The carbon dioxide sensor 502 measures the carbon dioxide concentration in the environment where the cell culture vessel 400 is placed, and transmits the measurement result to the device body 504.

The temperature sensor 503 measures the temperature in the environment (in the example shown in FIG. 2, in the culture solution 401) where the cell culture vessel 400 is placed. The temperature sensor 503 may be a general sensor for temperature measurement.

The device body 504 receives the measurement results from the respective sensors (the pH/turbidity sensor 501, the carbon dioxide sensor 502, and the temperature sensor 503). The device body 504 has a wireless communication function and transmits the respective measurement results to the control device 30 through the wireless communication function.

Incidentally, the carbon dioxide sensor 502 may not necessarily be configured to measure the carbon dioxide concentration of the culture solution 401, and may be any as long as it measures the carbon dioxide concentration in an arbitrary place in the culture environment (that is, in the sterile chamber 101). In this case, the carbon dioxide sensor 502 is configured to have a wireless communication function, and may be a separate housing from the pH/turbidity sensor 501 or the temperature sensor 503. Further, the carbon dioxide sensor 502 may be configured such that only one carbon dioxide sensor 502 is provided in the sterile chamber 101 and transmits the measurement result of the carbon dioxide concentration to the control device 30 through a built-in wireless communication function.

Similarly, the temperature sensor 503 may not necessarily be configured to measure the temperature of the culture solution 401, and may be any as long as it measures the temperature in an arbitrary place in the culture environment (that is, in the sterile chamber 101). In this case, the temperature sensor 503 is configured to have a wireless communication function, and may be a separate housing from the pH/turbidity sensor 501 or the carbon dioxide sensor 502. Further, the temperature sensor 503 may be configured such that only one temperature sensor 503 is provided in the sterile chamber 101 and transmits the measurement result of the temperature to the control device 30 through a built-in wireless communication function.

Incidentally, the sensing unit 50 may be configured to measure only necessary parameters according to the purpose of evaluation of the culture environment by the control device 30. That is, the sensing unit 50 may be configured to measure at least one of the pH of the culture solution 401, the carbon dioxide concentration in the sterile chamber 101, the temperature in the sterile chamber 101, and the turbidity of the culture solution 401. Further, the number of housings may be an arbitrary number.

Further, the sensing unit 50 may be configured to be connected to the control device 30 through a wire and transmit the measurement results thereto on condition that sterility is guaranteed. However, it is preferred that the sensing unit 50 has a wireless communication function because the sterility is easily guaranteed and also the device configuration is simplified.

In summary, the sensing unit 50 may be any as long as it measures the state of the culture environment (for example, at least one of the pH of the culture solution 401, the carbon dioxide concentration in the sterile chamber 101, the temperature in the sterile chamber 101, and the turbidity of the culture solution 401) and transmits the measurement result to the control device 30 regardless of wired or wireless connection. The sensing unit 50 may also be configured to measure another parameter which indicates the state of the culture environment without limiting to the above parameters (pH, carbon dioxide concentration, temperature, and turbidity).

The control device 30 receives the measurement results of the state of the culture environment from the sensing unit 50. The control device 30 evaluates the state in the culture environment (the internal space of the sterile chamber 101) based on the change in the measurement results over time. The evaluation as used herein refers to a concept not only including detection of an abnormality in the culture environment, but also including determination as to what state the culture environment is (for example, whether the state is a state immediately after cell seeding) even if the culture environment is in a normal state, or the like. Although the internal configuration of the control device 30 is not shown in the drawing, the control device 30 is configured to include a receiving unit which receives the state of the culture environment from the sensing unit 50, an evaluation unit which performs the below-mentioned evaluation of the culture environment based on the measurement result, and the like. Hereinafter, as a prerequisite for the evaluation of the control device 30, factors which change the respective parameters will be described with reference to FIGS. 3A to 3D.

Figure 3A:
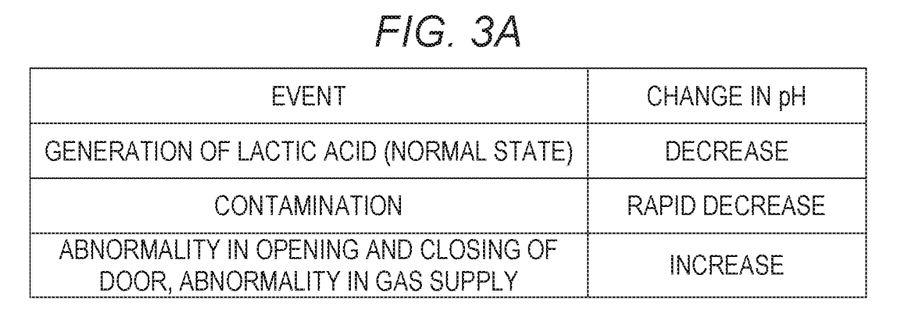
FIGS. 3A to 3D are views showing the relationship between a parameter and a change factor in a sterile space.
Figure 3B:
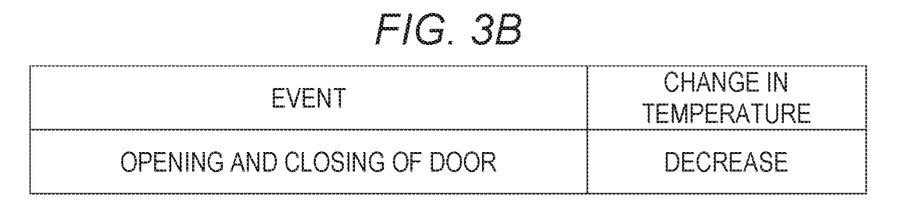
Figure 3C:
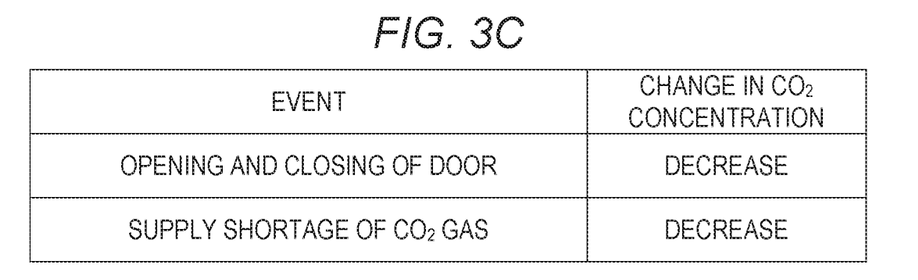

Firstly, a factor which changes the pH of the culture solution 401 will be described. In FIG. 3A, the relationship between each event (change factor) and a change in the pH is shown. In a normal cell culture process, lactic acid is generated by the metabolic activity of cells. Lactic acid shows a chemical reaction represented by the following formula (1) in the culture solution 401. Therefore, as the generation of lactic acid proceeds, acidification of the culture solution 401 is caused. In other words, the pH of the culture solution 401 decreases.

Formula (1)

When contamination occurs in the culture solution 401, bacteria or fungi in the culture solution 401 increase. Due to this increase in bacteria or fungi, lactic acid is rapidly generated. Therefore, when contamination occurs, acidification of the culture solution 401 rapidly proceeds. In other words, the pH of the culture solution 401 rapidly decreases.

A case where the pH of the culture solution 401 increases will be described. As described above, the carbon dioxide concentration in the sterile chamber 101 is maintained at a constant value (for example, 5%). Here, when the opening and closing of the opening and closing door 103 or an abnormality in the inflow of carbon dioxide gas from the carbon dioxide supply channel 113 occurs, the carbon dioxide concentration in the sterile chamber 101 decreases. Due to this, the amount of carbon dioxide to be dissolved in the culture medium also decreases, and alkalinization of the culture solution 401 proceeds (in other words, the increases).

Next, a factor which changes the internal temperature of the sterile chamber 101 will be described. Incidentally, in FIG. 3B, the relationship between each event (change factor) and a change in the temperature is shown. As described above, the internal temperature of the sterile chamber 101 is adjusted to be comparable to human body temperature (35 to 37° C.) by the air conditioner. Further, the temperature outside the sterile chamber 101 is maintained at usual room temperature (for example, about 20° C.). Therefore, when the opening and closing of the opening and closing door 103 occurs, air (35 to 37° C.) in the sterile chamber 101 flows out to the space outside the sterile chamber 101 (the space maintained at room temperature of about 20° C. in general). Due to this, the internal temperature of the isolator 10 decreases.

Next, a factor which changes the carbon dioxide concentration in the sterile chamber 101 will be described. Incidentally, in FIG. 3C, the relationship between each event (change factor) and a change in the carbon dioxide concentration is shown. As described above, the inside of the sterile chamber 101 is maintained in a state where the carbon dioxide concentration is high (for example, about 5% which is comparable to a human arterial blood carbon dioxide partial pressure) by the gas supply from the carbon dioxide supply channel 113. On the other hand, the carbon dioxide concentration outside the sterile chamber 101 is about 0.03% in the same manner as air. Here, when the opening and closing of the opening and closing door 103 occurs, the gas having a high carbon dioxide concentration flows outside the sterile chamber 101. Due to this, the carbon dioxide concentration inside the sterile chamber 101 decreases. Further, when an abnormality in the supply of carbon dioxide gas from the carbon dioxide supply channel 113 (supply shortage) occurs, the carbon dioxide concentration inside the sterile chamber 101 decreases.

Figure 3D:
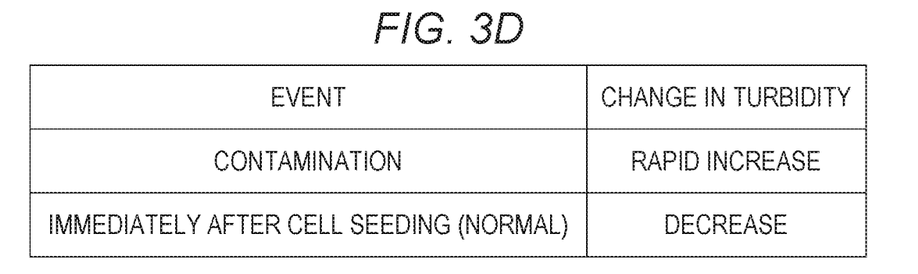

Next, a factor which changes the turbidity of the culture solution 401 will be described. When contamination occurs in the culture solution 401, bacteria or fungi penetrate into the culture solution 401. Due to the rapid proliferation of the bacteria or fungi, the turbidity of the culture solution 401 rapidly increases.

Incidentally, when cell seeding occurs, cells or contaminants are suspended in the culture solution 401, and therefore, the culture solution 401 becomes in a turbid state. As time passes from the cell seeding, the cells or contaminants precipitate, and therefore, the turbidity of the culture solution 401 decreases.

First Evaluation Method

Figure 4A:
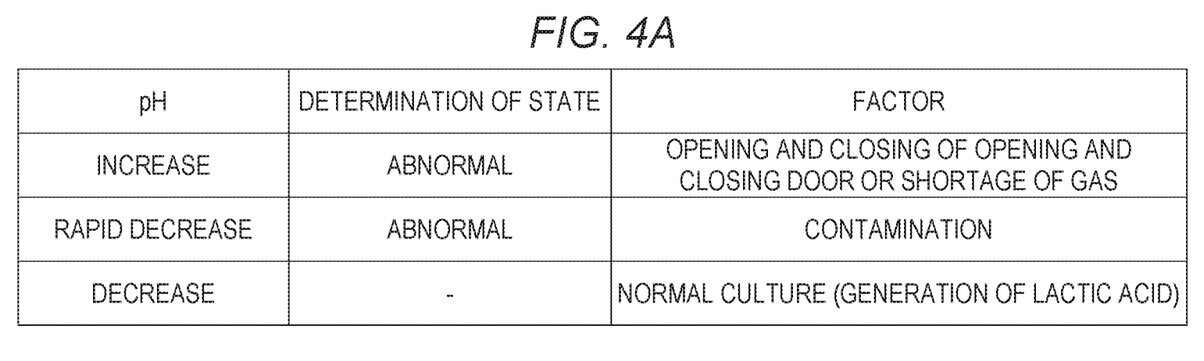
FIGS. 4A to 4C are views showing an evaluation method of a control device 30 according to the first embodiment.

In a first evaluation method, evaluation of the culture environment is performed by focusing on the change in the pH of the culture environment (culture solution 401) over time (the amount of change in a unit time). The evaluation method is shown in FIG. 4A.

The control device 30 receives the measured value of the pH one after another. Then, the control device 30 performs evaluation based on the change in the pH over time (the amount of change in a unit time). To be more specific, in a case where the pH has increased by more than the threshold value in a unit time (for example, in a case where the pH has increased by more than 0.10 in 1 hour), the control device 30 determines that an abnormality in the gas state (the state of carbon dioxide gas) in the culture environment has occurred. To be more specific, the control device 30 determines that the opening and closing of the opening and closing door 103 or an abnormality in the gas supply (the supply of carbon dioxide gas from the carbon dioxide supply channel 113) has occurred.

In a case where the pH has rapidly decreased in a unit time (which is a case where the pH has decreased by more than the threshold value which can be regarded as a rapid decrease in a unit time, and for example, in a case where the pH has decreased by more than 0.10 in 2 hours), the control device 30 determines that contamination has occurred in the culture solution 401. Further, in a case where the pH has decreased, although not rapidly, in a unit time (for example, in a case where the pH has decreased by only 0.00 to 0.05 in 5 hours), the control device 30 determines that the state is a state where appropriate cell culture is performed and lactic acid is generated.

In this manner, the control device 30 detects an abnormality in the gas state or contamination based on the change in the pH of the culture environment (culture solution 401) over time (the amount of change in a unit time).

Second Evaluation Method

Figure 4B:
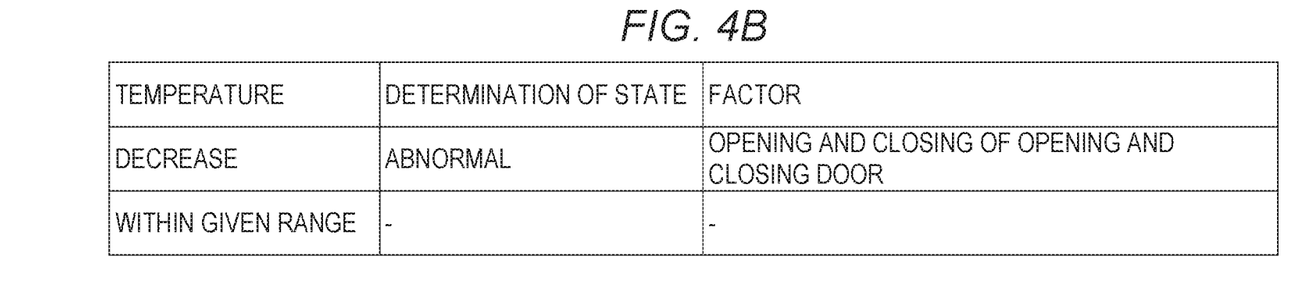

In a second evaluation method, evaluation of the culture environment is performed by focusing on the change in the temperature of the culture environment over time (the amount of change in a unit time). The evaluation method is shown in FIG. 4B.

The control device 30 receives the measured value of the temperature of the culture environment one after another. Then, the control device 30 performs evaluation based on the change in the temperature over time (the amount of change in a unit time). To be more specific, in a case where the temperature has decreased by more than a given value in a unit time (for example, in a case where the temperature has decreased by more than 1.0° C. in 1 minute), the control device 30 determines that the opening and closing of the opening and closing door 103 has occurred.

In this manner, the control device 30 detects whether or not the opening and closing of the opening and closing door 103 has occurred (an abnormality in the opening and closing of the opening and closing door 103) based on the change in the temperature of the culture environment (in the sterile chamber 101) over time (the amount of change in a unit time).

Third Evaluation Method

Figure 4C:
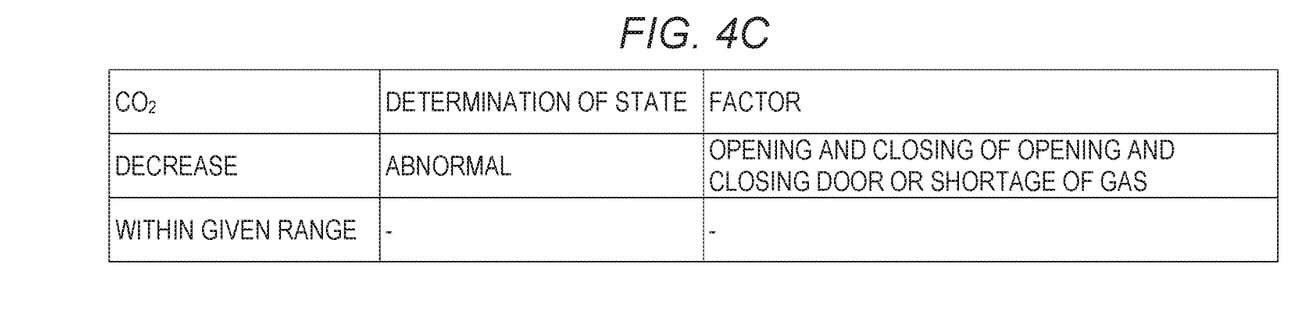

In a third evaluation method, evaluation of the culture environment is performed by focusing on the carbon dioxide concentration in the culture environment. The evaluation method is shown in FIG. 4C.

The control device 30 receives the measured value of the carbon dioxide concentration in the culture environment one after another. Then, the control device 30 performs evaluation of the culture environment based on the change in the carbon dioxide concentration over time (the amount of change in a unit time). To be more specific, in a case where the carbon dioxide concentration has decreased by more than a given value in a unit time (for example, in a case where the carbon dioxide concentration has decreased by more than 0.1% in 1 minute), the control device 30 determines that an abnormality in the gas state in the culture environment has occurred. To be more specific, the control device 30 determines that the opening and closing of the opening and closing door 103 has occurred or an abnormality in the gas supply (the supply of carbon dioxide gas from the carbon dioxide supply channel 113) has occurred.

On the other hand, in a case where the amount of change in the carbon dioxide concentration in a unit time is within a given range (for example, in a case where the change in the concentration in 1 minute is within 0.1%), the control device 30 determines that the opening and closing of the opening and closing door 103 or an abnormality in the gas supply does not occur.

In this manner, the control device 30 detects an abnormality in the gas state in the culture environment based on the change in the carbon dioxide concentration in the culture environment (in the sterile chamber 101) over time.

Fourth Evaluation Method

Figure 5A:
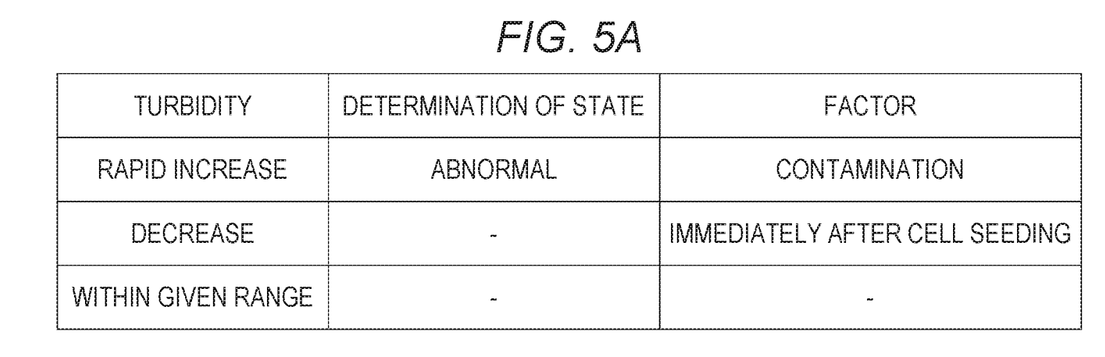
FIGS. 5A and 5B are views showing an evaluation method of the control device 30 according to the first embodiment.

In a fourth evaluation method, an abnormality is detected by focusing on the turbidity of the culture environment (culture solution 401). Incidentally, the evaluation method is also shown in FIG. 5A.

The control device 30 receives the measured value of the turbidity of the culture solution 401 one after another. Then, the control device 30 performs evaluation of the culture environment based on the change in the turbidity over time (the amount of change in a unit time). To be more specific, in a case where the turbidity has rapidly increased in a unit time (which is a case where the turbidity has increased by more than the threshold value which can be regarded as a rapid increase in a unit time, and for example, in a case where the turbidity has increased by more than 20% in 6 hours), the control device 30 determines that contamination has occurred.

On the other hand, in a case where the turbidity has decreased by more than a given value in a unit time (for example, in a case where the turbidity has decreased by more than 10% in 1 hour), the control device 30 determines that the state is a state immediately after cell seeding (determines that the state is not an abnormal state such as contamination).

On the other hand, in a case where the amount of change in the turbidity in a unit time is within a given range (for example, in a case where the amount of change in the turbidity in 1 hour is within 10%), the control device 30 determines that contamination or cell seeding does not occur.

In this manner, the control device 30 determines whether or not contamination or cell seeding occurs based on the change in the turbidity in the culture environment (in the sterile chamber 101) over time (the amount of change in a unit time).

In the above-mentioned first to fourth evaluation methods, an abnormality in the culture environment (the internal space of the sterile chamber 101) is detected using a single parameter (one of pH, temperature, carbon dioxide concentration, and turbidity), however, in the following fifth to seventh evaluation methods, an abnormality in the culture environment or the state thereof is detected in more detail using two parameters.

Fifth Evaluation Method

Figure 5B:
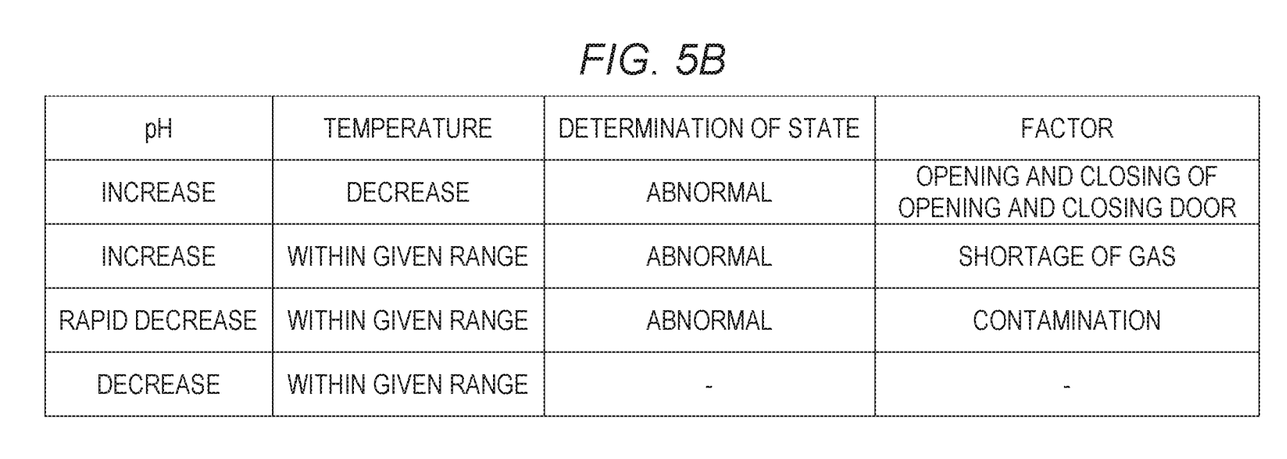

In a fifth evaluation method, evaluation of the culture environment is performed by focusing on both the pH and the temperature of the culture environment. The evaluation method is shown in FIG. 5B.

The control device 30 receives the measured value of the pH of the culture environment (culture solution 401) and the measured value of the temperature of the culture environment. Then, the control device 30 detects an abnormality in the gas state (the opening and closing of the opening and closing door 103 or an abnormality in the gas supply) and contamination based on the change in the pH over time (the amount of change in a unit time) in the same manner as the above-mentioned first evaluation method.

In a case where an abnormality in the gas state (the opening and closing of the opening and closing door 103 or an abnormality in the gas supply) is detected here, the control device 30 focuses on the change in the temperature in the culture environment. In a case where the temperature has decreased by more than a given value in a unit time, the control device 30 determines that the opening and closing of the opening and closing door 103 has occurred in the same manner as the above-mentioned second evaluation method. On the other hand, in a case where the amount of change in the temperature is within a given range in a unit time, the control device 30 determines that an abnormality in the supply of carbon dioxide gas has occurred.

In this manner, the control device 30 can also distinguish between the opening and closing of the opening and closing door 103 and the abnormality in the supply of carbon dioxide gas by referring also to the temperature in addition to the pH.

Sixth Evaluation Method

Figure 6A:
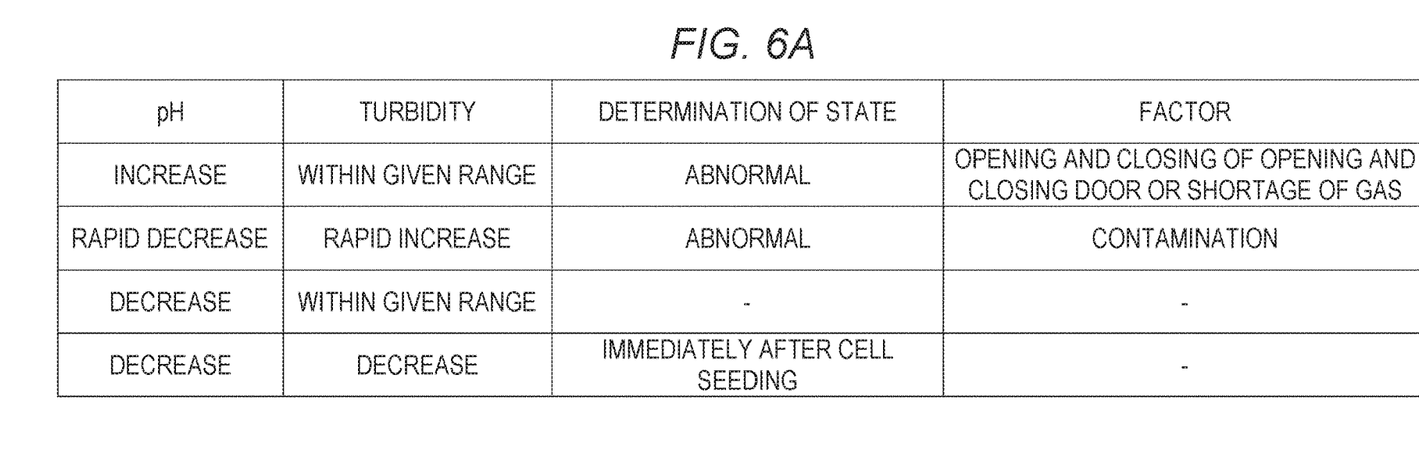
FIGS. 6A and 6B are views showing an evaluation method of the control device 30 according to the first embodiment.

In a sixth evaluation method, an abnormality is detected by focusing on both the pH and the turbidity of the culture environment. Incidentally, the evaluation method is also shown in FIG. 6A.

The control device 30 receives the measured value of the pH of the culture environment (culture solution 401) and the measured value of the turbidity of the culture environment (culture solution 401). Then, the control device 30 detects an abnormality in the gas state (the opening and closing of the opening and closing door 103 or the shortage of the gas) and contamination based on the change in the pH over time (the amount of change in a unit time) in the same manner as the above-mentioned first evaluation method.

Further, in a case where the pH decreases within a normal range (not a rapid decrease), the control device 30 focuses on the amount of change in the turbidity in a unit time. In a case where the turbidity has decreased by more than a given value in a unit time (for example, in a case where the turbidity has decreased by more than 10% in 1 hour), the control device 30 determines that the state is a state immediately after cell seeding. On the other hand, in a case where the amount of change in the turbidity in a unit time is within a given range, the control device 30 determines that the state is not a state immediately after cell seeding.

In this manner, the control device 30 can also determine whether or not the state is a state immediately after cell seeding in addition to the detection by the first evaluation method by also using the turbidity in addition to the pH.

Seventh Evaluation Method

Figure 6B:
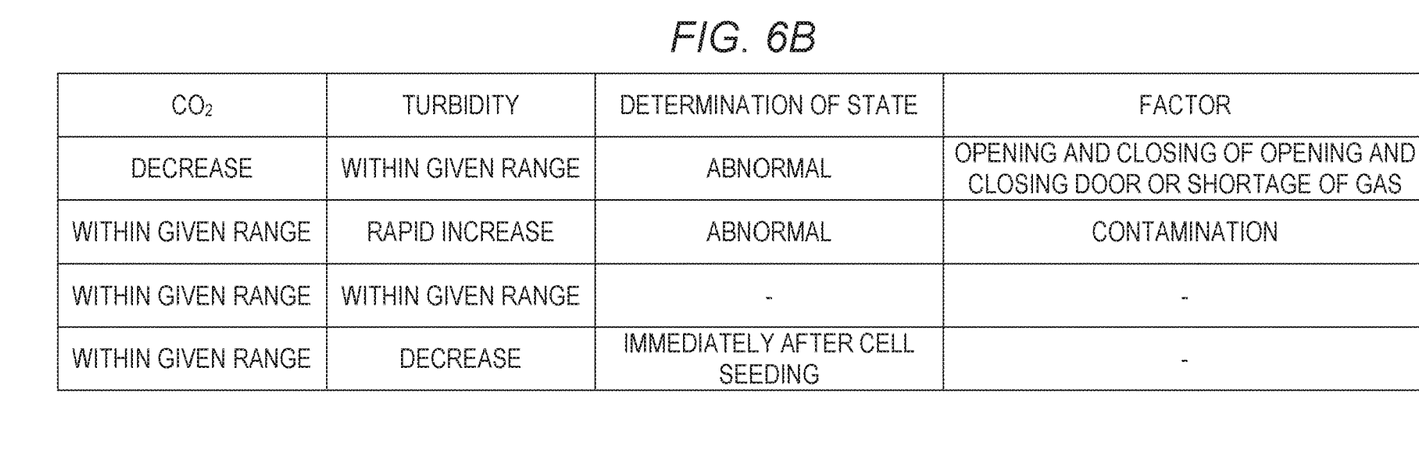

In a seventh evaluation method, evaluation of the culture environment is performed by focusing on both the carbon dioxide concentration and the turbidity of the culture environment. The evaluation method is shown in FIG. 6B.

The control device 30 receives the measured value of the carbon dioxide concentration in the culture environment (culture solution 401) and the measured value of the turbidity of the culture environment (culture solution 401). Then, the control device 30 detects the occurrence of contamination or cell seeding based on the change in the turbidity over time (the amount of change in a unit time) in the same manner as the above-mentioned fourth evaluation method.

Further, in a case where the carbon dioxide concentration has decreased by more than a given value in a unit time even if the amount of change in the turbidity in a unit time is within a given range, the control device 30 determines that an abnormality in the gas state (the opening and closing of the opening and closing door 103 or the shortage of the gas) has occurred.

In this manner, the control device 30 can also determine whether or not an abnormality in the gas state has occurred in addition to the detection by the fourth evaluation method by also using the carbon dioxide concentration in addition to the turbidity.

In the above-mentioned fifth to seventh evaluation methods, the control device 30 performs evaluation of the culture environment using two parameters. Incidentally, the control device 30 may perform a similar determination using a combination of two parameters different from the fifth to seventh evaluation methods.

Eighth Evaluation Method

Figure 7:
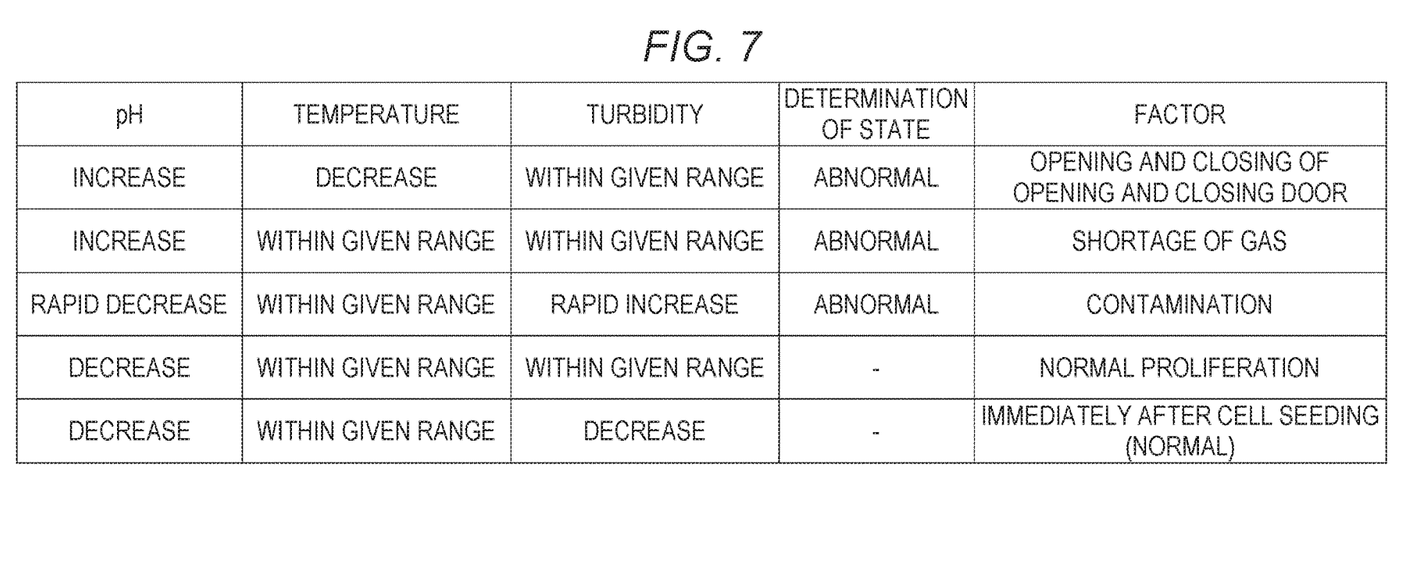
FIG. 7 is a view showing an evaluation method of the control device 30 according to the first embodiment.

Next, an example in which evaluation of the culture environment is performed using three parameters will be described. In an eighth evaluation method, evaluation of the culture environment is performed by focusing on the following three parameters: pH, temperature, and turbidity. The evaluation method is shown in FIG. 7.

The control device 30 receives the measured value of the pH in the culture environment (culture solution 401), the measured value of the temperature of the culture environment, and the measured value of the turbidity of the culture environment. Then, the control device 30 detects an abnormality in the gas state (the opening and closing of the opening and closing door 103 or the shortage of the gas) and contamination based on the change in the pH over time (the amount of change in a unit time) in the same manner as the above-mentioned first evaluation method.

In a case where an abnormality in the gas state has occurred, the control device 30 determines whether or not the temperature has decreased by more than a given value in a unit time. In a case where the temperature has decreased by more than a given value, the control device 30 determines that the abnormality in the gas state is attributed to the opening and closing of the opening and closing door 103. In a case where the amount of change in the temperature per unit time is within a given range, the control device 30 determines that the abnormality in the gas state is attributed to the supply of carbon dioxide gas from the carbon dioxide supply channel 113.

Further, in a case where the amount of change in the pH in a unit time is within a given range, the control device 30 focuses on the change in the turbidity in a unit time. In a case where the turbidity has decreased by more than a given value in a unit time (for example, in a case where the turbidity has decreased by more than 10% in 1 hour), the control device 30 determines that the state is a state immediately after cell seeding. On the other hand, in a case where the amount of change in the turbidity in a unit time is within a given range, the control device 30 determines that the state is not a state immediately after cell seeding.

The control device 30 can accurately distinguish among the following three abnormalities: an abnormality in the gas supply, the opening and closing of the opening and closing door 103, and contamination, and also can distinguish whether or not the normal state is a state immediately after cell seeding by focusing on the following three parameters: pH, temperature, and turbidity.

Ninth Evaluation Method

Figure 8:
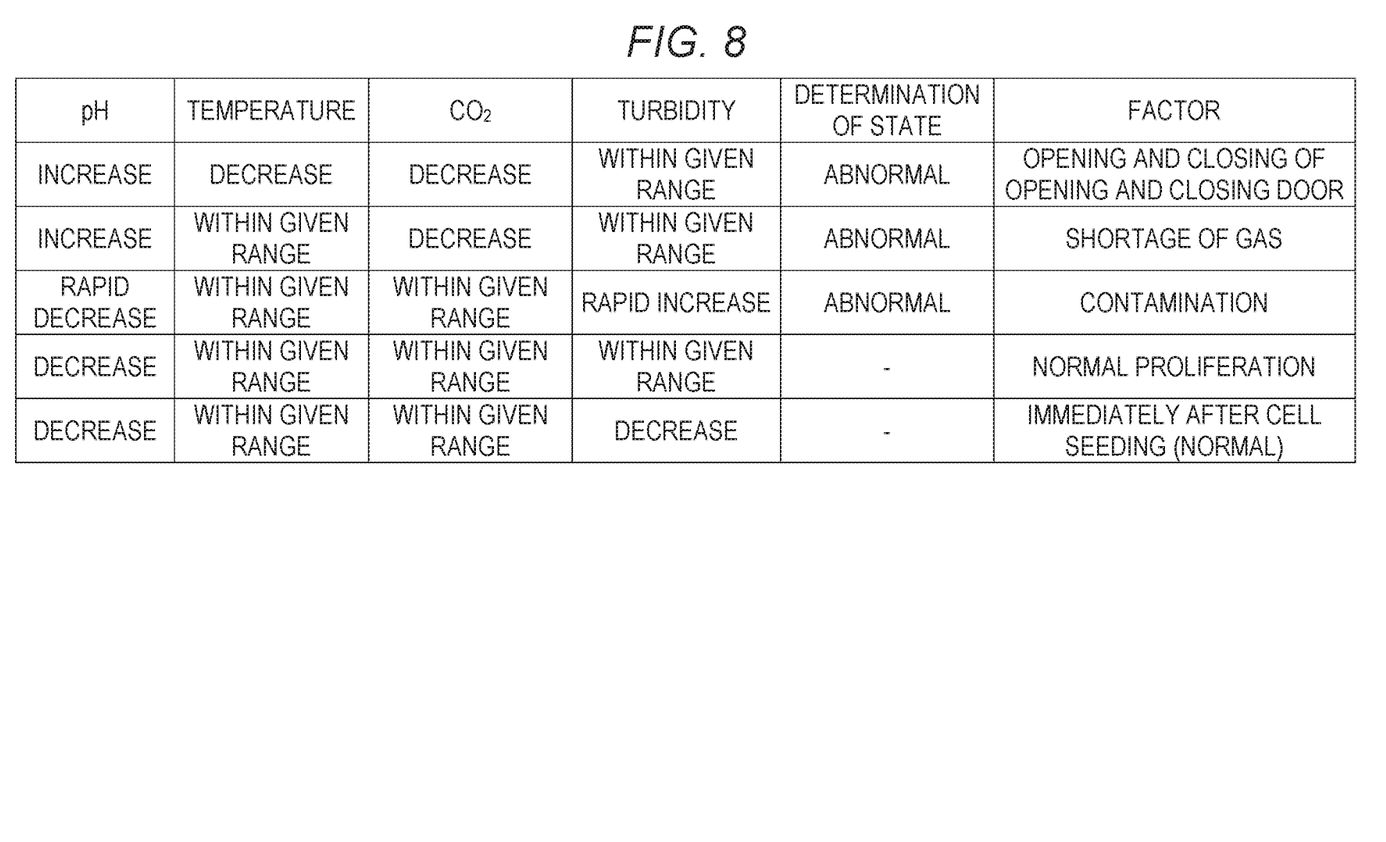
FIG. 8 is a view showing an evaluation method of the control device 30 according to the first embodiment.

Next, an example in which evaluation of the culture environment is performed using all the four parameters will be described. The evaluation method is shown in FIG. 8.

The details of the evaluation are exactly the same as the eighth evaluation method. However, the control device 30 may detect an abnormality in the gas state (the opening and closing of the opening and closing door 103 or an abnormality in the gas supply) by focusing not on the pH, but on the carbon dioxide concentration.

The control device 30 can accurately distinguish among the following three abnormalities: an abnormality in the gas supply, the opening and closing of the opening and closing door 103, and contamination, and also can distinguish whether or not the normal state is a state immediately after cell seeding by focusing on the following four parameters: pH, temperature, carbon dioxide concentration, and turbidity. Further, the control device 30 can detect an abnormality in the gas state (the opening and closing of the opening and closing door 103 or an abnormality in the gas supply) in consideration of both the pH and the carbon dioxide concentration, and therefore can detect an abnormality more accurately.

Incidentally, in the above-mentioned first to ninth evaluation methods, the following four parameters: pH, temperature, carbon dioxide concentration, and turbidity are mentioned, however, the control device 30 may also perform evaluation using a parameter (for example, the dissolved oxygen concentration or the glucose content in the culture solution 401, etc.) which indicates the state of the culture environment other than these.

The control device 30 desirably performs the above-mentioned evaluation at all times (that is, at all times while performing culture). According to this, it is possible to immediately detect the occurrence of an abnormality, and thus, it is possible to promptly take appropriate measures. Incidentally, in an environment where an abnormality does not often occur, the control device 30 may perform evaluation of the culture environment spottedly (in other words intermittently). Even if the evaluation is performed intermittently, the evaluation of the culture environment can be performed without taking out the culture vessel 400.

Next, an effect of the cell culture system 1 (or the control device 30) according to this embodiment will be described. As described above, the sensing unit 50 measures the state (pH, temperature, carbon dioxide concentration, turbidity, etc.) of the culture environment in the isolator 10 (the inside of the sterile chamber 101) and transmits the measurement result to the control device 30. The control device 30 performs evaluation of the culture environment (in the sterile chamber 101) based on the measurement result. That is, the control device 30 can perform evaluation in the culture environment without taking out the cell culture vessel 400 from the isolator 10. According to this, the cell culture system 1 can perform evaluation in the culture environment without applying a stress to the cells during culture.

The control device 30 may give an arbitrary notification (a notification by sound, display, email, or the like) when an abnormality in the culture environment is detected by the above-mentioned evaluation. According to this, an operator or a manager of the cell culture can recognize the occurrence of an abnormality in the culture environment, and can promptly take appropriate measures.

Further, the control device 30 may change the notification method according to the type of detected abnormality. According to this, an operator or a manager of the cell culture can immediately ascertain also the type of abnormality, and therefore can more promptly take appropriate measures.

Further, the control device 30 performs evaluation using the parameters (pH, temperature, carbon dioxide concentration, turbidity, etc.) strongly associated with the state of the culture environment, and therefore can appropriately evaluate the state of the culture environment.

In the above description, the control device 30 performs evaluation of the culture environment based on the change in the measurement result (pH, temperature, carbon dioxide concentration, turbidity, etc.) over time (the amount of change in a unit time). According to this, it becomes possible to detect an abnormality in consideration of the trend of change in the state in the culture environment. Incidentally, the control device 30 not only detects an abnormal state, but also may detect the deterioration of the culture environment, which cannot be said to be an abnormality, together when performing evaluation based on the change in the measurement result over time as described above. For example, in a case where the pH has decreased by more than 0.05 to 0.10 in 1 hour, the control device 30 determines that the state of the culture environment is deteriorated, although the state is not abnormal, and may output an alarm to indicate such a state. According to this, it is possible to take appropriate measures not only in a case where an abnormality occurs in the culture environment, but also before an abnormality occurs.

Further, the evaluation by the control device 30 is not limited to the evaluation based on the change in the measurement result over time. The control device 30 may perform evaluation of the culture environment by comparison of the measurement result with a predetermined threshold value. For example, the control device 30 may evaluate that an abnormality occurs in the culture environment when the pH is 7.5 or more or 7 or less. The control device 30 may give a notification (for example, output an alarm sound) to call attention when the measurement result deviates from a predetermined threshold value. For example, by outputting an alarm when the pH is 7 or less due to the metabolic activity of cells, an operator is prompted to replace the culture solution 401 in the cell culture vessel 400, and therefore, the slow-down of the culture speed or the like can be avoided. Further, the threshold value to be compared may be provided by being divided in several levels. For example, when the pH is 7.5 or more or 7 or less, the control device 30 may determine that an abnormality occurs in the culture environment, and when the pH is between 7.2 and 7, the control device 30 may determine that an abnormality does not occur, but the culture environment is being deteriorated. When an abnormality or a deterioration in the culture environment is detected, the control device 30 may output an alarm according to the detected level (an abnormality or a deterioration, although not an abnormality). According to this, it is possible to take appropriate measures not only in a case where an abnormality occurs in the culture environment, but also before an abnormality occurs. Incidentally, a structure of automatically replacing the culture solution 401 in the cell culture vessel 400 by some kind of method in a case where the control device 30 detects an abnormality or a deterioration in the culture environment may be provided. When an abnormality or the like occurs in the culture environment, the control device 30 may give a notification not only by alarm, but also by email, display on a display, or the like. That is, the control device 30 may be any as long as it performs evaluation of the culture environment based on the measurement result of the culture environment.

Further, the control device 30 may receive an input of various index values to be used for evaluation (detection of an abnormality or the like) from an operator or a manager (user) of the cell culture. The control device 30 may perform evaluation of the culture environment by comparison of the various index values with the measurement result. For example, an operator or a manager sets the abnormal value of the pH (for example, the pH is 7.5 or more) described above, or the decreasing rate of the pH (for example, the pH decreases by more than 0.1 per 2 hours) or the increasing rate of the turbidity (for example, the turbidity increases by more than 0.2% per 6 hours) for determining contamination. The control device 30 may determine the culture environment according to the set value. According to this, appropriate detection of an abnormality according to the type of cells, the purpose of culture, or the like can be realized.

Incidentally, in a case where there is no input from a user or the device is set not to accept any input, the control device 30 may perform evaluation of the culture environment using a default index value.

The control device 30 performs evaluation of the culture environment by performing the above-mentioned evaluation. Even in a case where the culture environment is normal, the control device 30 records the contents of the evaluation as appropriate. For example, the control device 30 writes the evaluation result in a data base or a log file on a file system as appropriate. The user can confirm that the culture state was normal by referring to this record (data in the data base or the log file). That is, the control device 30 may provide the above-mentioned evaluation result as an index for the validation of the culture environment.

Figure 9:
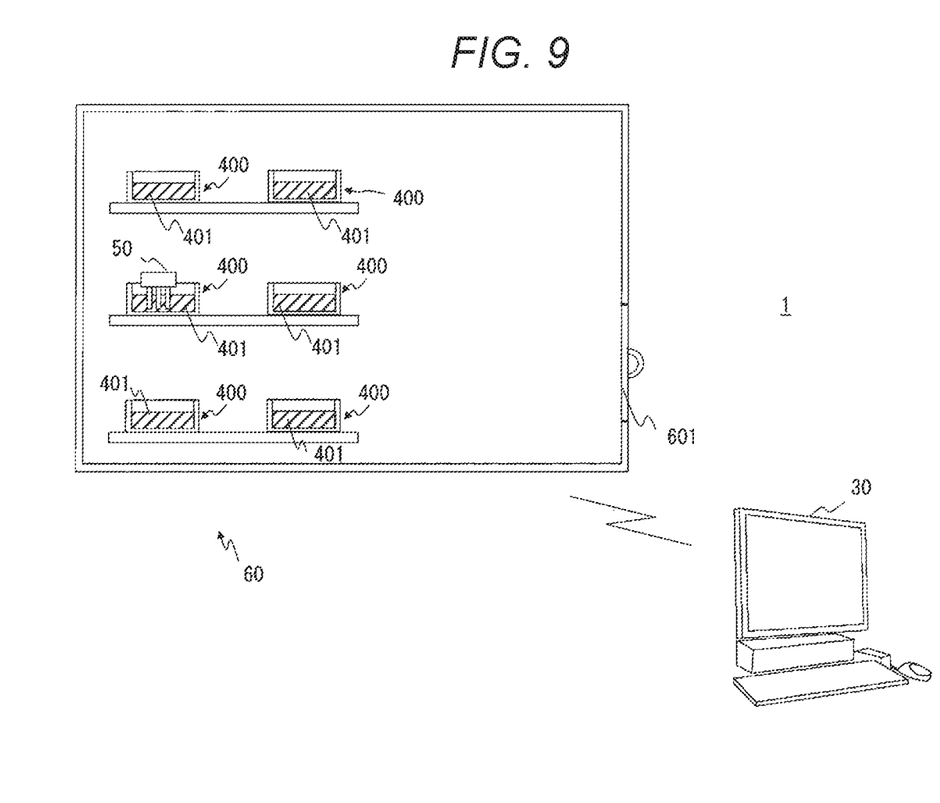
FIG. 9 is a conceptual view showing the configuration of the cell culture system 1 including an incubator 60 in place of an isolator 10.

In the above-mentioned description, the cell culture system 1 is described on the assumption that the cell culture system 1 includes the isolator 10, however, the cell culture system 1 may include another system other than an isolator system. FIG. 9 is a conceptual view showing the configuration of the cell culture system 1 including an incubator 60 in place of the isolator 10. The incubator 60 is one embodiment of the culture vessel housing chamber (the culture environment for housing the cell culture vessel having a culture solution containing cells to be cultured placed therein).

The incubator 60 is a space in which the cell culture vessel 400 containing the culture solution 401 is housed in the same manner as the above-mentioned isolator 10. An operator or a manager (user) of the cell culture opens an opening and closing door 601, takes out the cell culture vessel 400, and performs sampling or the like. In a case where the incubator 60 has a size such that a person can enter, a user may enter inside the incubator 60 and perform an operation. Also in the environment, a change in the temperature, contamination, a change in the pH, or the like can occur due to the opening and closing of the opening and closing door 601.

The sensing unit 50 measures the state of the culture environment and transmits the measurement result to the control device 30 in the same manner as the configuration shown in FIG. 1. The control device 30 performs evaluation of the culture environment (the inside of the incubator 60) using the above-mentioned evaluation methods (for example, FIGS. 4A to 8).

The isolator 10 shown in FIG. 1 or the incubator 60 shown in FIG. 9 is only an example of the culture vessel housing chamber, and the shape or the like (for example, the size, the number of opening and closing doors, the position of the opening and closing door, etc.) thereof may be arbitrary as long as it can house the cell culture vessel 400 and provide the culture environment. Further, the internal configuration of the sensing unit 50, the number of housings, and the data transmission system (wired or wireless) may be arbitrary.

A part or the entire of the above-mentioned processing of the control device 30 (to be more specific, the data reception of the measurement result from the sensing unit 50 and the evaluation processing of the culture environment described above) can be realized as a computer program which operates within the control device 30. The control device 30 is one embodiment of a computer including a CPU (Central Processing Unit), a hard disk, etc.

Here, the computer program is stored using various types of non-transitory computer readable media and can be supplied to the computer. The non-transitory computer readable media include various types of tangible storage media. Examples of the non-transitory computer readable media include magnetic recording media (for example, flexible disks, magnetic tapes, and hard disk drives), magneto-optical recording media (for example, magneto-optical disks), CD-ROM (Read Only Memory), CD-R, CD-R/W, semiconductor memories (for example, mask ROM, PROM (Programmable ROM), EPROM (Erasable PROM), flash ROM, and RAM (random access memory)). Further, the program may be supplied to the computer by various types of transitory computer readable media. Examples of the transitory computer readable media include electrical signals, optical signals, and electromagnetic waves. The transitory computer readable media can supply the program to the computer through a wired communication channel such as an electric wire or an optical fiber, or a wireless communication channel.

Hereinabove, the present disclosure made by the present inventor has been specifically described based on the embodiments, however, it should be understood that the present disclosure is not limited to the above-mentioned embodiments, and various modifications may be made thereto without departing from the gist of the present disclosure.

What is claimed is:

1. A cell culture system, comprising:
a culture vessel housing chamber configured to provide a culture environment for housing a cell culture vessel having a culture solution containing cells to be cultured placed therein;
a sensing unit configured to measure a state of the culture environment and configured to transmit a measurement result of the culture environment to an outside of the culture vessel housing chamber; and
a control device configured to receive the measurement result and configured to perform an evaluation of the culture environment based on the measurement result, wherein
the control device is configured to:
calculate a first evaluation value and a second evaluation value that are related to at least two of an amount of change in a hydrogen-ion exponent of the culture solution in a unit time, an amount of change in a carbon dioxide concentration in the culture environment in the unit time, an amount of change in a temperature in the culture environment in the unit time, and an amount of change in a turbidity of the culture solution in the unit time,
evaluate whether the culture environment is normal or abnormal based on a combination of the first evaluation value and the second evaluation value to calculate a factor of abnormality responsive to a determination that the culture environment is abnormal, and
determine that the culture environment is in a state immediately after cell seeding, responsive to the amount of change in the turbidity of the culture solution in the unit time decreases by more than a threshold even when it is determined that the culture environment is normal.

2. The cell culture system according to claim 1, wherein the control device is configured to give a notification when an abnormality in the culture environment or a deterioration of the state of the culture environment is detected.

3. The cell culture system according to claim 1, wherein the sensing unit is configured to measure at least one of the hydrogen-ion exponent of the culture solution, the carbon dioxide concentration in the culture environment, the temperature in the culture environment, and the turbidity of the culture solution, and
the control device is configured to detect an abnormality in the culture environment based on the measurement result of the sensing unit.

4. The cell culture system according to claim 3, wherein the control device is configured to detect a contamination or an abnormality in a gas state of the culture environment based on an amount of change in the hydrogen-ion exponent (pH) of the culture solution in the unit time.

5. The cell culture system according to claim 3, wherein the control device is configured to detect an abnormality associated with an opening and a closing of an opening and closing door provided in the culture environment based on the amount of change in the temperature in the culture environment in the unit time.

6. The cell culture system according to claim 3, wherein the control device is configured to detect an abnormality in a gas state of the culture environment based on the amount of change in the carbon dioxide concentration in the culture environment in a unit time.

7. The cell culture system according to claim 3, wherein the control device is configured to detect an occurrence of a contamination based on the amount of change in the turbidity of the culture solution in the unit time.

8. The cell culture system according to claim 3, wherein the control device is configured to perform the evaluation in the culture environment using an amount of change in two parameters of the hydrogen-ion exponent of the culture solution, the carbon dioxide concentration in the culture environment, the temperature in the culture environment, and the turbidity of the culture solution in the unit time.

9. The cell culture system according to claim 3, wherein the control device is configured to perform the evaluation in the culture environment using an amount of change in three parameters of the hydrogen-ion exponent of the culture solution, the carbon dioxide concentration in the culture environment, the temperature in the culture environment, and the turbidity of the culture solution in the unit time.

10. The cell culture system according to claim 3, wherein the control device is configured to perform the evaluation in the culture environment using an amount of change in the hydrogen-ion exponent of the culture solution, the carbon dioxide concentration in the culture environment, the temperature in the culture environment, and the turbidity of the culture solution in the unit time.

11. The cell culture system according to claim 1, wherein the control device is configured to perform the evaluation of the culture environment by receiving various index values to be used for the evaluation from a user and comparing the various index values with the measurement result.

12. A cell culture environment evaluation control device, which is configured to perform an evaluation of a culture environment for housing a cell culture vessel having a culture solution containing cells to be cultured placed therein, wherein the cell culture environment evaluation control device is configured to receive a measurement result of the culture environment from a sensing unit configured to measure a state in the culture environment and configured to perform the evaluation in the culture environment based on the measurement result, wherein the cell culture environment evaluation control device is configured to: calculate a first evaluation value and a second evaluation value that are related to at least two of an amount of change in a hydrogen-ion exponent of the culture solution in a unit time, an amount of change in a carbon dioxide concentration in the culture environment in the unit time, an amount of change in a temperature in the culture environment in the unit time, and an amount of change in a turbidity of the culture solution in the unit time, evaluate whether the culture environment is normal or abnormal based on a combination of the first evaluation value and the second evaluation value to calculate a factor of abnormality responsive to a determination that the culture environment is abnormal, and determine that the culture environment is in a state immediately after cell seeding, responsive to the amount of change in the turbidity of the culture solution in the unit time decreases by more than a threshold even when it is determined that the culture environment is normal.

* * * * *